US00PP15903P2

(12) United States Plant Patent
Whetman

(10) Patent No.: US PP15,903 P2
(45) Date of Patent: Aug. 2, 2005

(54) ***DIANTHUS* PLANT NAMED 'DEVON FLAVIA'**

(50) Latin Name: *Dianthus×hybrida*
Varietal Denomination: Devon Flavia

(76) Inventor: John Whetman, Deer Park Farm, TQ13 ONH Chudleigh (GB)

( * ) Notice: Subject to any disclaimer, the term of this patent is extended or adjusted under 35 U.S.C. 154(b) by 91 days.

(21) Appl. No.: 10/805,373

(22) Filed: Mar. 22, 2004

(51) Int. Cl.[7] ..... A01H 5/00

(52) U.S. Cl. ..... Plt./273

(58) Field of Search ..... Plt./273, 276, 272, Plt./281

*Primary Examiner*—Kent Bell

(57) ABSTRACT

A new cultivar of *Dianthus* plant named 'Devon Flavia' that is characterized by compact habit, medium-green foliage and fragrant flowers that are pink and reddish purple in color. In combination these traits set 'Devon Flavia' apart from all other existing varieties of *Dianthus* known to the inventor.

2 Drawing Sheets

Genus: *dianthus*. Species: ×*hybrida*.
Denomination: Devon Flavia.

BACKGROUND OF THE INVENTION

The present invention relates to a new and distinct cultivar of *Dianthus* or garden pink that is grown for use as an ornamental container plant. It is known botanically as *Dianthus×hybrida* and will be referred to hereinafter by the cultivar name 'Devon Flavia'.

'Devon Flavia' is the product of a breeding program started by the inventor in 1980 in a cultivated area of Houndspool, Dawlish, Devon, United Kingdom. The primary focus of the breeding program is to produce new cultivars of garden pinks that exhibit unique characteristics of flower color and form, and which, preferably, are highly and pleasantly fragrant. In addition, new varieties are selected for being well-proportioned in respect of ratio of overall height (including flower canopy) to overall width.

'Devon Flavia' exhibits pink and reddish-purple flowers, mounding habit and medium-green foliage, and is used as an ornamental container plant. Cultural requirements include full sun, well-drained soil and moderate water.

'Devon Flavia' is a hybrid plant that resulted from the open pollination of a population of plants of the inventor's introduction known as *Dianthus* 'Devon Glow' (unpatented). 'Devon Flavia' was selected a single plant by the inventor, in 2000. The male and female parents of 'Devon Flavia' are presumed to be *Dianthus* 'Devon Glow'. When compared with the flowers of *Dianthus* 'Devon Glow', the flowers of Devon Flavia are lighter pink ('Devon Glow' has lavender colored flowers), more fully double ('Devon Glow' is semi-double), and more sweetly perfumed.

Asexual reproduction of the new cultivar was first accomplished by the inventor in 2000 in a cultivated area of Houndspool, United Kingdom. The method of asexual propagation used was stem cuttings. Since that time the characteristics of the new cultivar have been determined stable and are reproduced true to type in successive generations by vegetative propagation.

SUMMARY OF THE INVENTION

The following traits have been repeatedly observed and represent the characteristics of the new *Dianthus* cultivar 'Devon Flavia'. These traits in combination distinguish this cultivar from all other commercial varieties known to the inventor. 'Devon Flavia' has not been tested under all possible conditions and phenotypic differences may be observed with variations in environmental, climatic and cultural conditions, without however any change in genotype.

1. *Dianthus* 'Devon Flavia' exhibits a compact habit.
2. *Dianthus* 'Devon Flavia' exhibits sweetly-scented double flowers that are pink and reddish-purple in color.
3. *Dianthus* 'Devon Flavia' exhibits medium-green foliage.
4. *Dianthus* 'Devon Flavia' is 20–30 cm. in height and 10–15 cm in width at maturity.
5. *Dianthus* 'Devon Flavia' is an evergreen perennial herb.
6. *Dianthus* 'Devon Flavia' blooms from March to November.
7. *Dianthus* 'Devon Flavia' is hardy to minus 15° Centrigrade.

BRIEF DESCRIPTION OF THE DRAWINGS

The accompanying color drawings illustrate the overall appearance of the new *Dianthus* variety 'Devon Flavia' showing colors as true as it is reasonably possible to obtain in colored reproductions of this type. Colors in the drawings may differ from the color values cited in the detailed botanical description, which accurately describe the actual colors of the new variety 'Devon Flavia'.

The drawing labeled as FIG. 1 illustrates 'Devon Flavia' in flower.

Figure 1:
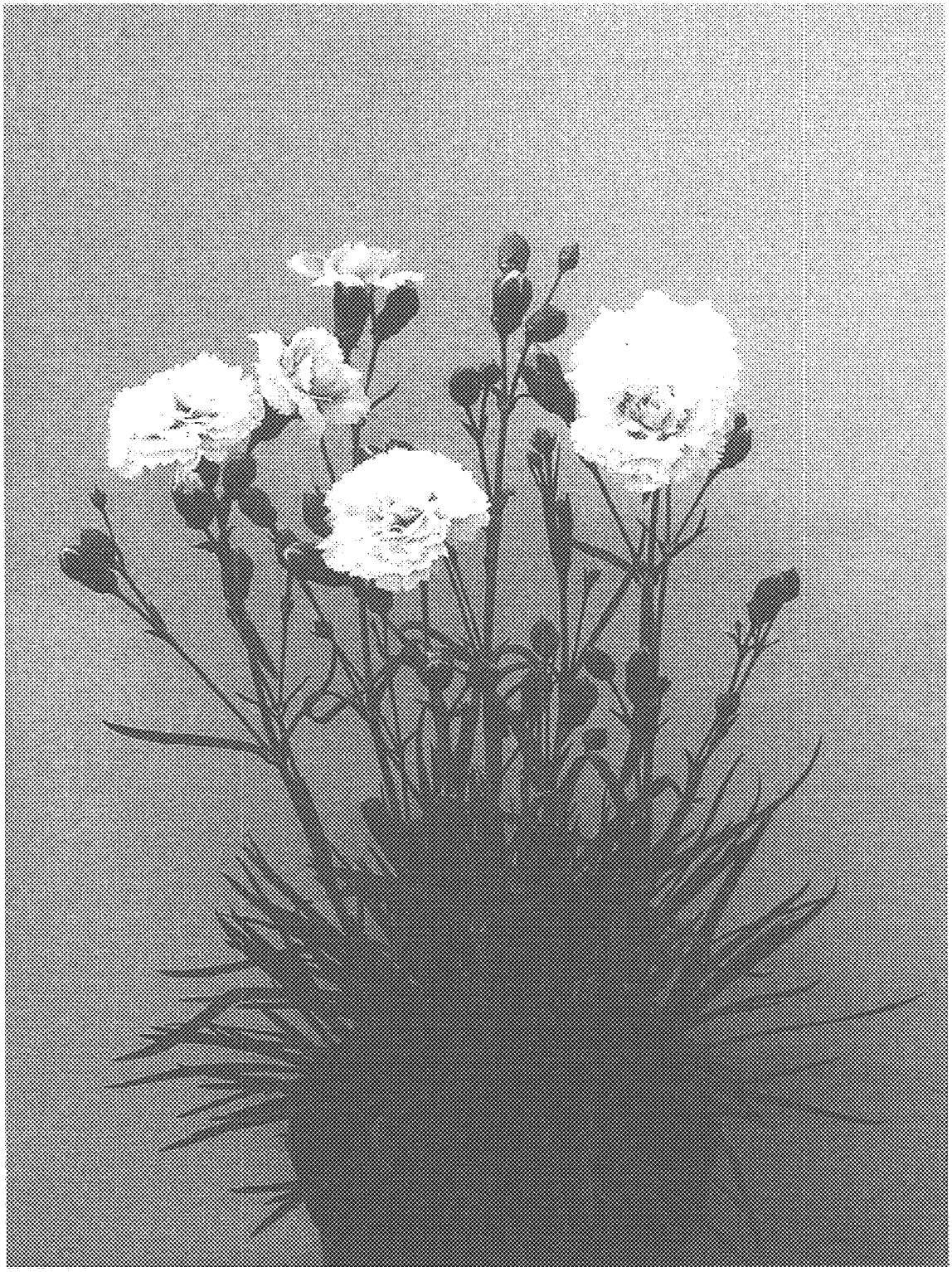
Figure 2:
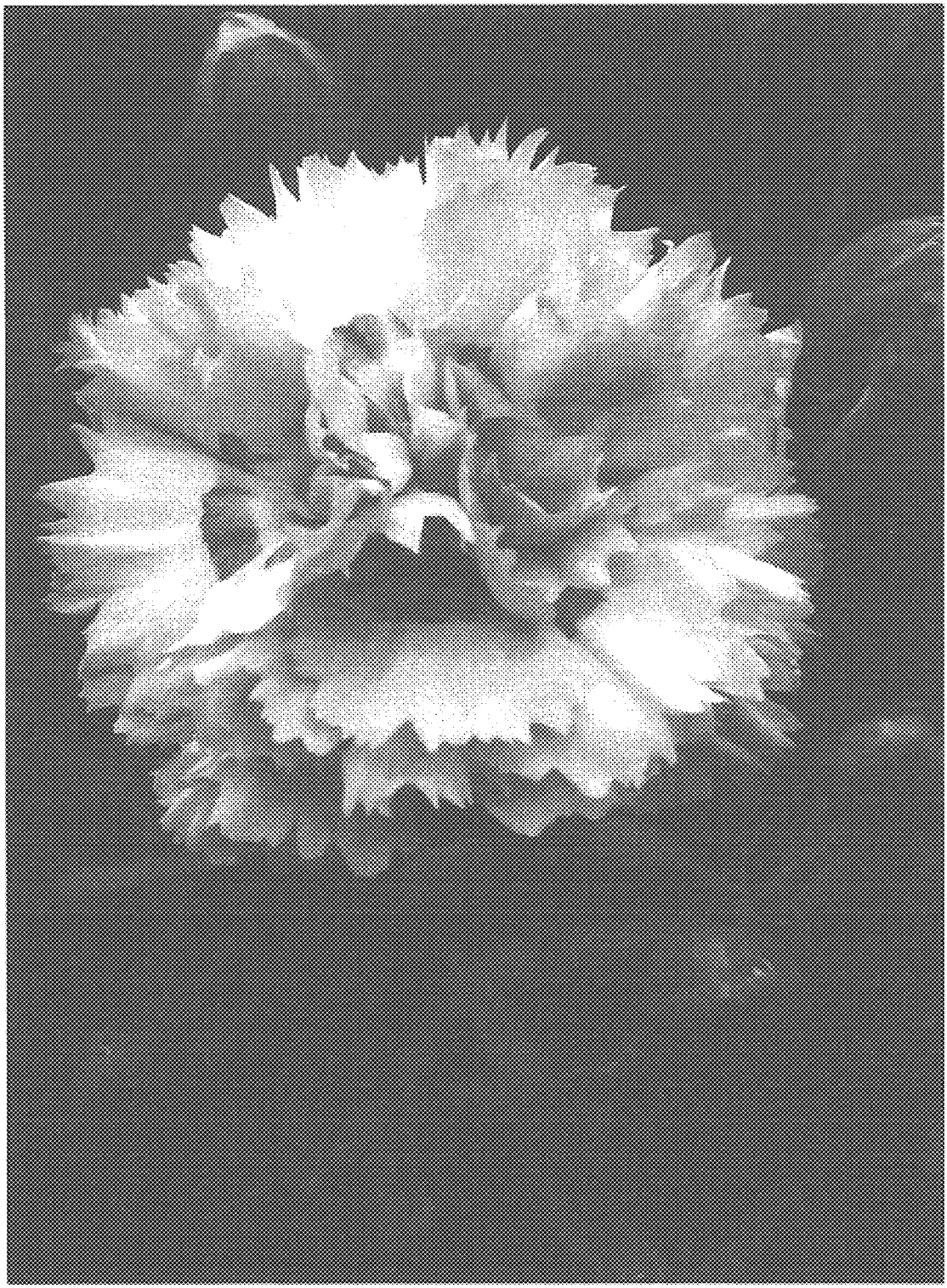

The drawing labeled as FIG. 2 illustrates a close-up of a typical flower of 'Devon Flavia'.

All drawings were made of 5-month-old plants grown in 1.5-liter containers under a cold glasshouse in Houndspool, Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Flavia'. Data was collected during spring from plants grown in 1-liter containers under a cold glasshouse in Houndspool, United Kingdom. The observed plants were approximately nine months old having been grown from cuttings taken in late summer of the previous year. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus* 'Devon Flavia'.
Species: ×*hybrida*.
Common name: Hybrid garden pink.
Commercial classification: Hardy perennial.
Use: Ornamental plant for pots and containers.
Parentage: 'Devon Flavia' is a hybrid plant that resulted from the open pollination of a group of *Dianthus* plants named *Dianthus* 'Devon Glow'.
- *Presumed female parent plant.*—*Dianthus* 'Devon Glow'.
- *Presumed male parent plant.*—*Dianthus* 'Devon Glow'.

Plant description:
- *Bloom period.*—March to November.
- *Plant habit.*—Compact habit.
- *Plant height.*—20–30 cm. in height at maturity.
- *Plant width.*—10–15 cm. in width at maturity.
- *Plant hardiness.*—Hardy to minus 15° Centrigrade.
- *Type.*—Perennial herb.
- *Root system.*—Fibrous.
- *Propagation.*—Propagation is accomplished using stem cuttings.
- *Cultural requirements.*—Plant in full sun, well-drained and moderately fertile soil and keep well fertilized and watered.
- *Diseases and pests.*—Susceptible to known *Dianthus* pests and disease but no other susceptibilities to pests or disease are known to the inventor.
- *Time required to produce a rooted cutting.*—2 weeks are needed to produce a rooted cutting and 5 weeks to produce a plug plant.
- *Temperature recommended for cuttings to produce roots.*—The air temperature needed to produce a rooted cutting, is a minimum of 15° Centigrade, and a base heat of 21° Centigrade.
- *Crop time.*—4–6 months is needed to produce a finished 1-liter plant from a well-rooted cutting.

Stem:
- *Shape.*—Cylindrical.
- *Stem dimensions.*—Maximum of 23–26 cm. in length and 2–3 mm. in diameter.
- *Stem surface.*—Glabrous and glaucous.
- *Stem color.*—N138A.
- *Branching.*—Numerous basal breaks and racemose inflorescence.
- *Internode length.*—15–60 mm. between nodes.
- *Node dimensions.*—2 mm. in diameter and 5 mm. in length.
- *Node color.*—144C.

Foliage:
- *Type.*—Evergreen.
- *Shape.*—Lanceolate.
- *Division.*—Simple.
- *Apex.*—Acute.
- *Base.*—Decurrent.
- *Venation.*—Not prominent.
- *Margins.*—Entire.
- *Attachment.*—Sheathing.
- *Arrangement.*—Opposite and spiraling on stem.
- *Surfaces* (*adaxial and abaxial*).—Glaucous.
- *Leaf dimensions.*—10–12 cm. in length and 4–5 mm. in width.
- *Leaf color* (*adaxial surfaces*).—N138A.
- *Leaf color* (*abaxial surfaces*).—N138B.
- *Stipules.*—2 present.
- *Stipule dimensions.*—3 mm. in width and 4 mm. in length.
- *Stipule color.*—N138A.
- *Anthocyanin.*—Absent.
- *Fragrance.*—Absent.

Flowers:
- *Inflorescence.*—Raceme with branches.
- *Flower type.*—Double and symmetrical.
- *Flower shape.*—Salviform.
- *Flower dimensions* (*including calyx*).—35 mm. in length and 40 mm. in diameter.
- *Bud color.*—Colors N138A and 143C are individually present.
- *Anthocyanin.*—Absent.
- *Bud dimensions.*—20 mm. in length and 10 mm. in width.
- *Bud shape.*—Rhomboid.
- *Petals.*—Persistent, apopetalous, overlapping.
- *Petal apex.*—Rounded, slightly flattened.
- *Petal base.*—Tapers to narrow base of width approximately 2 mm.
- *Petal number including petaloid stamens.*—25–40, of which: Number of petals: approximately 15 to 20. Number of petaloid stamens: approximately 10 to 20.
- *Petal dimensions.*—35 mm. in length and 16–18 mm. in width.
- *Petal margin.*—Irregularly dentate.
- *Petal shape.*—Obdeltoid.
- *Petal color* (*adaxial surface*).—Individual colors of 62B on ground of blade, N66B on band across blade, 65C on middle of strap, and 150C on base of strap.
- *Petal color* (*abaxial surface*).—Individual colors of 73C on ground of blade, band across blade and middle of strap, and 150C on base of strap.
- *Petal surfaces* (*adaxial and abaxial surfaces*).—Glabrous.
- *Petaloid dimensions.*—Variable, approximately 15 mm in length and 20 mm in width.
- *Petaloid shape.*—Very irregular, often folded and twisted on vertical axis.
- *Petaloid apex.*—Irregular, folded; apical margin serrate; lateral margins smooth.
- *Petaloid base.*—Narrows to approximately 2 mm in width.
- *Coloration of petaloids* (*abaxial surface*).—As for petals but predominantly 62B, 65C, and base 150C.

*Coloration of petaloids* (*adaxial surface*).—As for petals: 73C and base 150C.

*Calyx dimensions.*—18–20 mm. in width and 13–15 mm. in length.

*Sepal color* (*adaxial surfaces*).—Individual colors N138A and 143C.

*Sepal color* (*abaxial surfaces*).—A combination of colors N138A and 143C.

*Sepal surface.*—Glaucous.

*Sepal apex.*—Acuminate.

*Sepal margins.*—Smooth.

*Anthocyanin.*—Absent.

*Sepal number.*—5 in number.

*Fused or unfused.*—Fused.

*Epicalyx number.*—4 opposite pairs of bracts.

*Epicalyx shape.*—Elliptic; apex acuminate; base decurrent; margin smooth.

*Epicalyx dimensions.*—6 mm. in length and 7 mm. in width.

*Epicalyx color* (*adaxial surfaces of both pairs*).—N138A.

*Epicalyx color* (*abaxial surfaces of both pairs*).—N138A.

*Anthocyanin.*—Absent.

*Peduncle dimensions.*—15–25 mm. in length and 1–2 mm. in diameter.

*Peduncle color.*—N138A.

*Peduncle surface.*—Glaucous.

*Fragrance.*—Medium sweet perfume.

*Lastingness of flower.*—Outdoors, on growing plant at ambient 10° C., 15 days; at 20° C., 10 days Indoors as cut flower: 7–10 days.

Reproductive organs:

*Stamens.*—Ranges from 0–5 in number from flower to flower.

*Stamen color.*—150D.

*Stamen dimensions.*—15–18 mm. in length and 1 mm. in diameter.

*Anther color.*—155B.

*Anther dimensions.*—2 mm. in length and 1 mm. in diameter.

*Anther attachment.*—Dorsifixed.

*Pollen color.*—N66D.

*Quantity of pollen.*—Minute amount.

*Styles.*—2 in number.

*Style dimensions.*—20 mm. in length and 1 mm. in width.

*Style color.*—155B.

*Pistils.*—2 per flower.

*Stigma color.*—N66D.

*Stigma number.*—Two in number.

*Stigma form.*—Bifid.

*Height of stigma above petals* (*at maturity*).—Exserted 5 mm.

*Ovary position.*—Superior.

*Ovary dimensions.*—7 mm. in height and 5 mm. in diameter.

*Ovary shape.*—Spindle shaped.

*Ovary color.*—144C.

Seed:

*Seed.*—Absent. No seed has been observed to date.

It is claimed:

1. A new and distinct cultivar of *Dianthus* plant named 'Devon Flavia' as described and illustrated herein.

* * * * *